United States Patent
Bolenbaugh

[19]

[11] Patent Number: 6,132,359
[45] Date of Patent: Oct. 17, 2000

[54] BRACHYTHERAPY SEEDS

[75] Inventor: David W. Bolenbaugh, Wheeling, Ill.

[73] Assignee: Nycomed Amersham plc, Buckinghamshire, United Kingdom

[21] Appl. No.: 09/226,685

[22] Filed: Jan. 7, 1999

[51] Int. Cl.[7] .............................. A61M 36/00; A61N 5/00
[52] U.S. Cl. ............................................................. 600/8
[58] Field of Search ................................................ 600/1–8

[56] References Cited

U.S. PATENT DOCUMENTS

| | | | |
|---|---|---|---|
| 1,753,287 | 4/1930 | Failla | 600/8 |
| 2,429,438 | 10/1947 | Wappler | 600/8 |
| 3,351,049 | 11/1967 | Lawrence | 600/8 |
| 3,438,365 | 4/1969 | Packer et al. | 600/8 |
| 4,323,055 | 4/1982 | Kubiatowicz | 128/1.2 |
| 4,702,228 | 10/1987 | Russell, Jr. et al. | 600/8 |
| 4,784,116 | 11/1988 | Russell, Jr. et al. | 600/8 |
| 4,891,165 | 1/1990 | Suthanthiran | 600/8 |
| 5,163,896 | 11/1992 | Suthanthiran et al. | 600/8 |
| 5,342,283 | 8/1994 | Good | 600/8 |
| 5,460,592 | 10/1995 | Langton et al. | 600/7 |
| 5,949,082 | 9/1999 | Schubert et al. | 250/493.1 |
| 5,997,463 | 12/1999 | Cutrer | 600/8 |

*Primary Examiner*—Cary O'Connor
*Assistant Examiner*—Catherine McPherson
*Attorney, Agent, or Firm*—Marshall, O'Toole, Gerstein, Murray & Borun

[57] ABSTRACT

An improved brachytherapy seed having (a) a casing for encapsulating a radioactive material, wherein a center portion of the casing has a diameter that is substantially larger than the diameter of two end portions of the casing, and/or (b) a carrier for the radioisotope, wherein the carrier has a polygonal cross section, and, optionally, one end of the carrier is rotated around the longitudinal axis of the carrier.

23 Claims, 6 Drawing Sheets

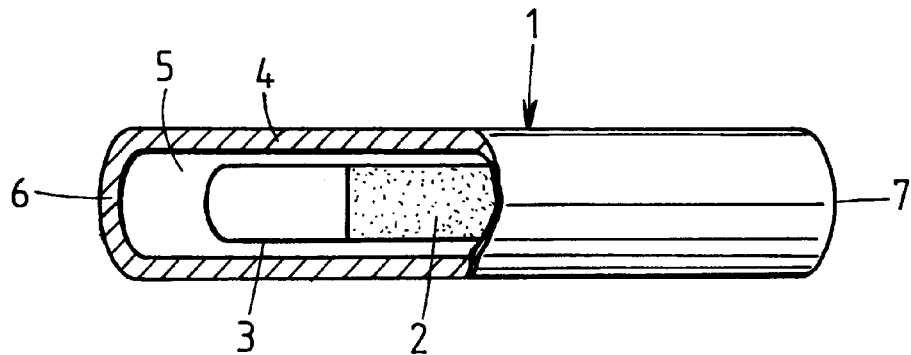
Fig. 1 PRIOR ART
Fig. 2
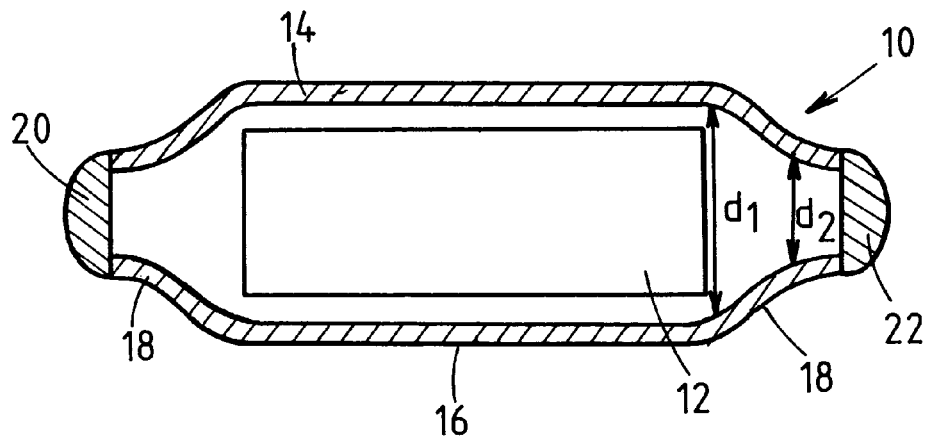
Fig. 3
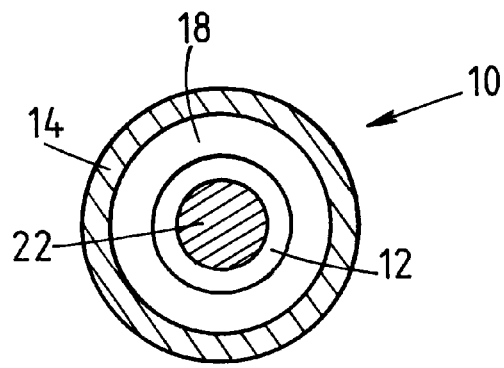

BRACHYTHERAPY SEEDS

FIELD OF THE INVENTION

The present invention relates to improved brachytherapy seeds used in therapeutic medical treatments. In particular, the present invention relates to radioactive brachytherapy seeds comprising: (a) a carrier for a radioisotope, wherein the carrier has a polygonal cross section and one end of the carrier is rotated along its longitudinal axis, and/or (b) a casing for encapsulating the carrier having a center portion of the casing and two end portions, wherein the center portion has a substantially larger diameter than the end portions of the casing.

BACKGROUND OF THE INVENTION

Radiation therapy is the treatment of diseases, especially the treatment of tumors, including malignant tumors, with radiation. In radiation therapy, the ultimate aim is to destroy the malignant tissue without causing excessive radiation damage to nearby healthy, and possibly vital, tissue. This is difficult to accomplish because of the proximity of malignant tissue to healthy tissue.

Medical personnel and investigators have developed methods for preferentially irradiating deep seated diseased tissue as opposed to healthy tissue. These methods include the use of high energy X-ray beams together with cross fire and rotational techniques which create a radiation pattern that is maximized at the site of the diseased tissue. Nonetheless, some absorption and damage inevitably occurs to healthy tissue in the path through which radiation passes to arrive at deep seated diseased tissue.

One method of limiting the zone of irradiation utilizes radioactive articles in the form of small, radioactive "seeds," which are permanently implanted at the zone to be irradiated. Such seeds contain a radioactive source disposed within a sealed capsule. The seeds are injected or implanted into body tissue at the site to be treated. The small size of therapeutic seeds allows the seeds to be inserted within the tissue to be treated, in order to totally surround the tissue.

The advantages of interstitial implantation of a radiation-emitting article for localized tumor treatment have long been recognized. Interstitially implanted articles concentrate the radiation at a zone where radiation treatment is needed, i.e., near or within a tumor in order to directly affect surrounding tumor tissue, while exposing normal, healthy tissue to substantially less radiation than beaming radiation into the body from an external source.

Implanting radioactive articles directly into solid tumors to destroy the tumors is a therapy referred to as brachytherapy (i.e., short-range therapy). This form of therapy permits the application of larger doses of radiation directly to the tumor.

Radioactive seeds are disclosed, for example, in Lawrence U.S. Pat. No. 3,351,049 and Kubiatowicz U.S. Pat. No. 4,323,055. The seeds comprise a tiny sealed capsule having an elongate cavity containing the radioisotope, e.g., iodine-125 or palladium-103, adsorbed onto a carrier body. Because of the low energy X-rays emitted by iodine-125 and the short half-life of iodine-125, the seeds can remain implanted in the tissue of a patient indefinitely without excessive damage to surrounding healthy tissue or excessive exposure to other individuals near the patient.

In order to function effectively, the radiation emitted from the radioisotope within the seed cannot be blocked or otherwise unduly attenuated. Preferably, radiation emitted from the radioisotope is uniformly distributed from the seed in all directions, i.e., has an isotropic radial distribution. In particular, it is generally desirable to avoid seeds having end constructions having a greater concentration of radiation-absorbing material, which attenuates the therapeutic radiation required for the successful treatment of diseased tissue.

Providing a uniform distribution of radiation from a seed has been difficult to impossible to accomplish. For example, present-day seeds have a radioisotope adsorbed onto a carrier substrate, which is placed into a metal casing that is welded at the ends. The most advantageous materials of construction for the casing which encapsulates the radioisotope-laden carrier are stainless steel, titanium, and other low atomic number metals. However, problems exist with respect to sealing casings made from these materials. Such metallic casings typically are sealed by welding, but welding of such small casings is difficult because welding can locally increase the casing wall thickness, or can introduce higher atomic number materials at the ends of the casing where the welds are located. The presence of such localized anomalies can significantly alter the geometrical configuration at the welded ends, resulting in undesirable shadow effects in the radiation pattern emanating from the seed. Such seeds also have the disadvantage of providing a nonhomogeneous radiation dose to the target due to their construction, i.e., the relatively thick ends attenuate the radiation more than the relatively thin body of the seed.

Other methods of forming the seed casing include drilling a metallic block to form a casing, and plugging the casing to form a seal. However, this method suffers from the disadvantage that a casing of uniform wall thickness is difficult to obtain, and the radiation source, therefore, is not able to uniformly distribute radiation.

Several patents are directed to implantable radioactive seeds for use in brachytherapy. Examples of such patents include Kubiatowicz U.S. Pat. No. 4,323,055; Suthanthiran U.S. Pat. No. 4,891,165; Russell, Jr. et al. U.S. Pat. No. 4,784,116; Lawrence U.S. Pat. No. 3,351,049; Good U.S. Pat. No. 5,342,283; and Langton et al. U.S. Pat. No. 5,460,592. Although these patents illustrate improvements in construction of seeds for use in brachytherapy, the art seeds still suffers from the problem of providing a seed that, simultaneously, (a) is easy to manufacture, (b) provides adequate protection against leakage of radioactivity, and, importantly, (c) provides a uniform radiation dose in all directions. Significant advances have been made with respect to ease of seed manufacture and protection against leakage of radioactivity from the seed. The present invention is directed to providing a brachytherapy seed having these two attributes, and the additional attribute of providing a more uniform dose of radiation in all directions.

SUMMARY OF THE INVENTION

The present invention is directed to improved brachytherapy seeds. More particularly, the present invention is directed to brachytherapy seeds that provide a more uniform radiation dose in the treatment of a disease, like cancer.

Accordingly, one aspect of the present invention is to provide an improved casing for encapsulating a carrier having a radioisotope applied thereto. The improved casing allows a more uniform radiation dose to be delivered to the target site, i.e., a malignant tumor.

Another aspect of the present invention is to provide a casing for a brachytherapy seed that is elongated in shape, and has a center portion of a first diameter and end portions of a second diameter, wherein the second diameter is substantially smaller than the first diameter.

Another aspect of the present invention is to provide a cylindrical casing for a brachytherapy seed having a center portion and two end portions, wherein the diameter of each end portion, independently, is about 25% to about 80% less than the diameter of the center portion.

Yet another aspect of the present invention is to provide a casing for an elongated brachytherapy seed wherein the radiation dose emanating from the seed is essentially uniform along the elongated body of the seed and from the ends of the seed.

Another aspect of the present invention is to provide brachytherapy seeds having an improved carrier for radioisotopes. The improved carrier has a shape that permits a more uniform dose of radiation to emanate from the seed.

Another aspect of the present invention is to provide an elongated brachytherapy seed containing a rod-like carrier for the radioisotope, wherein the carrier has a geometrical shape that provides a more uniform radiation dose to the target site both through the longitudinal body of the seed and through the ends of the seed.

Yet another aspect of the present invention is to provide a brachytherapy seed comprising a casing and a carrier having a radioisotope applied thereto. The casing is generally cylindrical in shape, and the carrier is of a dimension and shape to fit within the cylindrical casing and essentially fill the entire cavity of the cylindrical casing. In accordance with an important aspect of the present invention, the carrier has a polygonal cross section.

One further aspect of the present invention is to provide a radioisotope carrier for use in brachytherapy seeds, wherein the carrier is acicular, i.e., rod-like, in shape, and has a polygonal cross section. In particular, the carrier has a polygonal cross section, wherein the polygon has three to six sides.

Yet another aspect of the present invention is to provide an acicular radioisotope carrier for a brachytherapy seed having a rectangular, square, or pentagonal cross section.

Another aspect of the present invention is to provide an acicular radioisotope carrier for a brachytherapy seed having a polygonal cross section, wherein the acicular carrier is rotated about one end of its longitudinal axis.

A further aspect of the present invention is to provide a brachytherapy seed having a radioisotope-laden carrier within a casing, wherein the carrier is acicular in shape, is polygonal in cross section, and has one end rotated from 1° to about 180° about the longitudinal axis of the carrier to more fully fill the cavity within the casing and to provide a more uniform dose of radiation emanating from the seed, especially through the ends of the seed.

Still another aspect of the present invention is to provide a brachytherapy seed comprising a casing and a radioisotope-laden carrier disposed within the casing, wherein (a) the casing is generally cylindrical in shape and has a center portion of a first diameter and end portions of a second diameter, wherein the second diameter is substantially smaller than the first diameter, and (b) the radioisotope-laden carrier is acicular, of a polygonal cross section, and has one end rotated about the longitudinal axis of the carrier.

These and other aspects of the invention will become apparent from the following detailed description of the preferred embodiments, taken in conjunction with the figures.

BRIEF DESCRIPTION OF THE DRAWINGS

FIG. 1 is a partially cut-away side view of a present-day brachytherapy seed;

FIG. 2 is a cut-away side view of an embodiment of a brachytherapy seed of the present invention;

FIG. 3 is an end view of the seed of FIG. 2;

DETAILED DESCRIPTION OF THE PREFERRED EMBODIMENTS

Figure 4A:
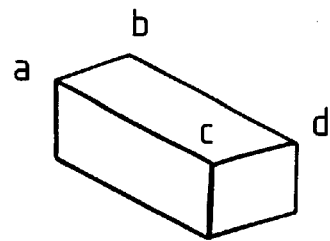
FIGS. 4(a) and (b) are perspective views of a carrier for a brachytherapy seed.

Brachytherapy is a form of radiation therapy wherein a radioactive source is positioned near, or within, a radiation target, e.g., a tumor. The radioactive source is delivered in the form of a seed containing a radioisotope that has been applied to a carrier substrate. The radioisotope-laden carrier is encapsulated by, and sealed within, a suitable metal casing.

Various radioisotopes have been used in brachytherapy, and several factors are considered when deciding which radioisotope is used for a particular therapy. These factors include the type and intensity of radiation emanating from the radioisotope, the half-life of the radioisotope, and the particular disease being treated. The decision also encompasses considerations of efficacy of the therapy, safety to surrounding healthy tissue, and safety to medical personnel that handle and implant the brachytherapy seeds.

The threshold radiation dose required to treat a particular disease, such as a cancer, is an important parameter in designing the brachytherapy seed. Because a threshold dosage must reach the tumor for effective treatment, and because the radiation emanating from the radioisotope within the seed is attenuated, the amount of radioisotope applied to the carrier typically is significantly greater than the amount needed to provide the threshold dosage.

A significant percentage of the radiation emitted from a brachytherapy seed is attenuated and unavailable for therapeutic purposes. For example, the carrier absorbs a significant portion of the emitted radiation, and the casing further attenuates radiation emanating from the seed. In addition, prior seed designs suffer in having casing ends that are thicker than the casing body. This construction results in an uneven radiation dose emanating from the seed as a whole. Accordingly, the amount of radioisotope applied to the carrier is increased such that the seed as a whole emits at least the threshold radiation dose necessary to treat the disease.

It would be desirable, therefore, to provide a brachytherapy seed wherein the amount of radioisotope that is applied to the carrier (which necessarily is in excess of the amount needed to provide a threshold therapeutic dose of radiation) can be reduced, while still providing the threshold dose. Reducing the amount of radioisotope on the carrier, while maintaining the threshold radiation dose to treat the disease, has several advantages, including safety to personnel that manufacture, handle, and implant the seeds, and significant cost savings.

One route to reducing the amount of radioisotope that is applied to the carrier is to provide a brachytherapy seed that more uniformly emits radiation over its entire geometry. A uniform radiation emission from the body and ends of a seed reduces the amount of radioisotope needed to provide a therapeutic dose because the seed does not have any relatively "cold" spots, like the ends of the seed. Hence, the seed does not require as large an excess of radioisotope, and the seed as a whole provides a therapeutic radioactive dose to the target.

The present invention is directed to improved brachytherapy seeds that provide a more uniform radiation dose over the entire geometry of the seed. The present seeds improve therapy efficacy, and can lead to a reduction in the amount of radioisotope applied to the carrier. The present brachytherapy seeds contain an improved seed casing and/or an improved carrier.

With respect to casings, prior brachytherapy seeds suffer from having casing ends that are thicker than the casing body. Accordingly, the amount of radiation emanating from the ends of the seed is less than the amount of radiation emanating from the body of the seed. An example of a present-day brachytherapy seed is illustrated in FIG. 1, wherein a seed 1 contains a therapeutic amount of a radioisotope 2 disposed on a carrier 3. The radioisotope-laden carrier 3 is disposed in a cavity 5 of a cylindrical casing 4. Casing 4 is sealed at ends 6 and 7, typically by welding. The sealing operation typically results in a seed 1 having welded ends 6 and 7 that are thicker than the material of construction of casing 4.

The present invention is directed to casings that help overcome the disadvantages associated with prior casings for brachytherapy seeds. In accordance with an important feature of the present invention, the brachytherapy seed casings comprise an elongated tube, and typically a cylindrical tube, that is open at each end. Each end of the tube is swaged such that that tube has a center portion of a first diameter and end portions of a second diameter, wherein the second diameter of the ends is substantially less than the first diameter of the center portion. The two ends of the casing can have the same diameter or a different diameter, but each diameter is substantially smaller than the first diameter of the center portion of the casing.

FIG. 2 illustrates a present brachytherapy seed 10 having a radioisotope-laden carrier 12 encapsulated by a casing 14. Casing 14 is a tube having a center portion 16 and two end portions 18. Center portion 16 has a diameter $d_1$ that is substantially larger than the diameter $d_2$ of end portions 18. One method of manufacturing brachytherapy seed 10 comprises swaging one end portion 18 of casing 14, then plasma discharge welding swaged end portion 18 to provide a weld seal 20. The radioisotopeladen carrier 12 then is disposed in the cavity of casing 14, and the second end portion 18 of casing 14 then is swaged and plasma discharge welded to provide a weld seal 22, thereby encapsulating carrier 12. Alternatively, carrier 12 can be disposed in the center portion 16 of casing 14, followed by swaging ends 18, then plasma discharge welding ends 18 to provide weld seals 20 and 22 to encapsulate carrier 12.

In accordance with an important feature of the present invention, the diameter $d_2$ of end portions 18 is smaller than the cross section of carrier 12. This permits radiation emitted by the radioisotope to more readily emanate from the end portions 18 of seed 10. This feature is illustrated in FIG. 3. FIG. 3 is an end view of seed 10 showing that the smaller diameter end portions 18 provide an expanded area for radiation to emanate from the ends of seed 10, and thereby provide a more uniform radiation dose from seed 10.

A brachytherapy seed casing of the present invention is manufactured from a cylindrical tube of a metal that is suitable for use as a brachytherapy seed casing. The casing is constructed from a material that provides adequate thin wall strength, and that readily allows radiation to pass uniformly through the material. The thin walls permit a larger carrier to be disposed in the seed. The material of construction of the casing also does not corrode when in contact with body fluids.

Suitable casing materials are metals, and typically low atomic numbered metals, such as stainless steel alloy or titanium. Higher atomic number metals, such as gold or platinum, attenuate too much radiation emanating from the radioisotope-laden carrier to be useful per se. However, higher atomic numbered metals are useful as a plating over various low atomic number materials, such as beryllium, which otherwise is too toxic if used without an outer coating. Other suitable casing materials include, but are not limited to, tantalum, nickel alloys, copper alloys, and aluminum alloys.

Titanium, which has a low atomic number and a high strength-to-weight ratio, is the preferred casing material. Titanium is exceptionally corrosion-resistant, and is satisfactory from the standpoint of tissue compatibility and nontoxicity. Preferably, the titanium is a pure alloy to assure good working properties. The wall thickness of a titanium casing can be about 0.001 to about 0.005 inch (about 0.025 to about 0.127 mm), with radiation attenuation being about 7% per thousandth of an inch. An optimum wall thickness for a titanium casing is about 0.002 inch (0.051 mm).

The cylindrical tube, such as a titanium tube, of uniform diameter is swaged at each end to provide a tube having a center portion of a first diameter and end portions of a second diameter, wherein the second diameter is substantially less than the first diameter. In particular, the diameter of each end portion of the swaged tube, independently, is about 25% to about 80% less than the diameter of the center portion of the tube. If the ends are swaged to provide a less than about 25% diameter reduction, the reduction is not sufficient to provide a significant improvement in uniformity of radiation emissions from the seed. If the ends are swaged to provide a greater than about 80% diameter reduction, seed production problems result with respect to disposing the radioisotope-laden carrier into the casing, and with respect to sealing the casing ends by standard techniques such as plasma discharge, laser, electron beam, or tungsten inert gas (TIG) welding. In addition, if diameter reduction at the casing ends is too great, manufacture of the brachytherapy seed becomes difficult.

Preferably, the cylindrical casing tube is swaged to provide ends having a diameter that is about 35% to about 70% less than the diameter of the center portion of the casing. To achieve the full advantage of the present invention, the ends of the casing tube are swaged to provide ends having a diameter that is about 40% to about 60% less than the diameter of the center portion of the tube.

Each swaged end of the casing has a length that is about 10% to about 20% of the total length of the casing. Accordingly, the center portion of the casing, which has the larger diameter, constitutes about 60% to about 80% of the total length of the seed casing.

If the carrier has a diameter that is smaller than the diameter of the swaged ends, then the carrier can be inserted into the casing after both ends are swaged. However, preferred brachytherapy seeds contain a radioisotope-laden carrier that substantially fills the cavity within the casing.

Such an embodiment provides a larger dose of radiation, thereby requiring fewer seeds in the brachytherapy treatment. Therefore, in embodiments wherein the carrier has a diameter greater than the diameter of the swaged ends, the carrier is inserted into the casing prior to swaging and sealing one or both of the ends.

A brachytherapy seed having a casing illustrated in FIG. 2, for example, exhibits an improvement over prior seeds because welds 20, 22 at ends 18 of the seed are small, and radiation, therefore, can emanate from ends 18 of the seed and pass around welds 20, 22 to provide a more uniform radiation dose. In particular, the diameter of carrier 12 in seed 10 of FIG. 2 is greater than the diameter of welds 20, 22, and radiation can emanate from carrier 12 through casing 14 at center portion 16 and at swaged ends 18.

The overall size of a brachytherapy seed casing of the present invention can be identical to casings presently used in brachytherapy seeds. In particular, the casing is designed for implantation by perforate penetration or injection, e.g., by hypodermic needle or similar device especially designed for positioning brachytherapy seeds. Therefore, the casing has a relatively narrow maximum outer diameter of about 0.25 to about 1 millimeter, and about 0.25 to about 25 millimeters in length. For permanent implantation, as by hypodermic injection, the outside diameter of the seed is preferably about 0.80 millimeter and is small enough to pass through a 17-gauge hypodermic needle. The seed typically is about 4 to 5 mm long. Such seeds exhibit minimal movement in the tissue and do not migrate from the area where they are implanted.

A brachytherapy seed of the present invention also can include an improved radioisotope-laden carrier. Typically, the carrier used in present-day seeds is a cylindrical metallic rod having a treated surface to which the radioisotope of choice is applied. The carrier serves primarily as a solid substrate on which a radioisotope is uniformly distributed. The carrier also often serves as an X-ray marker to enable medical personnel to properly position the seeds near or in the target site, and to scan the patient at a later date to determine whether the seeds have moved from the target site.

Prior carriers had a circular or near circular cross section. The diameter of the carrier was sufficiently small such that the carrier could be disposed into a seed casing, but also was sufficiently large such that the cavity of the seed casing is substantially filled by the carrier. In such an arrangement, only the circular cross sectional area of the carrier was positioned to emit radiation through the ends of the seed.

The relatively small circular cross sectional area of the carrier, plus the relatively large thickness of the ends of the seed, substantially reduces the amount of radiation emanating from the ends of the seed compared to the amount of radiation emanating from the longitudinal body of the seed. The present carrier is designed such that the cross sectional area of the carrier and a portion of the longitudinal surfaces of the carrier are positioned to emit radiation through the ends of the seed.

Therefore, in accordance with an important feature of the present invention, the carrier is acicular and has a polygonal cross section. In particular, the carrier has a trigonal, quadrilateral, pentagonal, or hexagonal cross section. Preferred carriers have a quadrilateral or pentagonal cross section. The quadrilateral cross section can be rectangular or square. Polygonal cross sections of greater than about six sides do not provide the improvements achieved by three- through six-sided polygons because such cross sections begin to approximate a circular cross section.

In preferred embodiments, the acicular carrier has one end rotated about the longitudinal axis of the carrier. The carrier typically has one end rotated about 1° to about 180°, and preferably about 20° to about 150°, around the longitudinal axis the carrier. To achieve the full advantage of the present invention, the carrier has one end rotated about 45° to about 120° around the longitudinal axis of the carrier. Rotating one end of the carrier around its longitudinal axis has the effect of exposing a portion of each longitudinal surface to the ends of the seed, which contributes to, and therefore increases, the amount of radiation emitted from the ends of the seed.

FIG. 4(a) illustrates a carrier of the present invention having a square cross section prior to rotating one end of the carrier around the longitudinal axis of the carrier. The corners of the top surface of carrier of FIG. 4(a) are denoted a, b, c, and d.

Figure 4B:
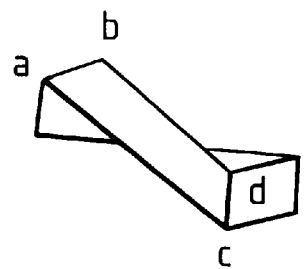

FIG. 4(b) illustrates the carrier of FIG. 4(a) after rotating one end of the carrier 90° around the longitudinal axis of the carrier. The positions of corners a, b, c, and d have changed such that the four corners are no longer in the same plane, as in FIG. 4(a), but are in different planes.

Figure 5A:
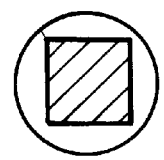
FIGS. 5(a) and (b) are cutaway end views of a brachytherapy seed containing a carrier of FIG. 4(a) and FIG. 4(b), respectively.

The net effect of rotating one end of a carrier of polygonal cross section is to expose a portion of each longitudinal surface of the carrier to the ends of the seed. This is illustrated in FIG. 5, wherein FIG. 5(a) illustrates the end view of a seed having the carrier of FIG. 4(a) disposed in a seed casing. In FIG. 5(a), the only surface of the carrier that is exposed to the end of the seed is the cross sectional surface area of the carrier.

Figure 5B:
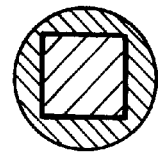

FIG. 5(b) illustrates an end view of a seed having the carrier of FIG. 4(b) disposed in a seed casing. In FIG. 5(b), the cross sectional area of the carrier is exposed to the end of the seed, and, in addition, a portion of each longitudinal surface of the carrier also is exposed to each end of the seed. The overall result is that more radiation is emitted through the ends of the seed in FIG. 5(b) as opposed to the seeds in FIG. 5(a) and in the prior art. The improved carriers of the present invention, therefore, provide a more uniform radiation emission from all surfaces of the brachytherapy seed. In addition, the carrier more fully fills the cavity of the casing, as illustrated by comparing FIG. 5(b) to FIG. 5(a), A carrier of the present invention can be constructed of any material that serves as a solid support for the radioisotope of choice. The carrier ensures that the radioisotope is substantially evenly distributed throughout the length of the seed. It is preferred that the carrier is constructed from a material that is detectable by X-rays. When the carrier functions both as the carrier for the radioisotope and the X-ray marker, manufacture of the seeds is greatly simplified. Furthermore, because the carrier generally conforms to the shape of the capsule, the exact location and orientation of the seed in the tissue can be determined from X-ray photographs.

The carrier, therefore, can be constructed from any material to which the requisite therapeutic amount of radioisotope can be attached, and preferably, that is detectable by X-rays. The typical material is silver or copper. The carrier is acicular in shape and has a polygonal cross section of a suitable length and diameter for easy disposition into a seed casing, and to occupy a substantial portion of the casing cavity. The carrier is preferably about 3 mm long and 0.5 mm in diameter (maximum) when used in a standard titanium casing having a length of 4.5 mm and an exterior diameter of 0.8 mm. A 3 mm long carrier results in minimum shifting within the casing while allowing adequate room to weld the ends of the casing without adversely affecting the carrier. The diameter of the carrier is about 0.10 mm to about 0.70 mm (the maximum inside diameter of the conventional titanium casing). The preferred diameter is about 0.5 mm, which provides good X-ray visibility, is relatively easy to handle during seed manufacture, and slides easily into the seed casing without abrading against the interior walls of the casing.

Silver and copper are the materials of choice for the carrier because these metals provide good X-ray visualization and because commonly used radioactive isotopes, such as iodine and palladium, can be easily attached to a silver or copper surface by chemical or electroplating processes. Other X-ray opaque metals, such as gold and iron, for example, can be used as a carrier for purposes of the present invention. Likewise, a suitable metal can be deposited (chemically or by using "sputtering" and "ion plating" techniques) onto a substrate other than a metal, e.g., a polypropylene filament, preferably such that the thickness of the metallic coating on the substrate exceeds about 0.050 mm to ensure X-ray visualization.

The radioactive isotope attached to the surface of the carrier is not limited. Nonlimiting examples of useful radioisotopes include iodine-125, palladium-103, cesium-131, gold-198, thulium-170, chromium-56, arsenic-73, yttrium-90, and mixtures thereof. In addition, radioactive isotopes of samarium, tantalum, radon, radium, cobalt, iridium, and mixtures thereof, also can be used in the present brachytherapy seeds. Other gamma ray emitting elements and radioactive isotopes, including mixtures of one or more radiation sources capable of emitting therapeutically useful forms of radiation (e.g., gamma rays, alpha particles, beta particles, Auger electrons, X-rays, and electromagnetic waves) also are contemplated as useful in the practice of the present invention, provided they are presented in a form and in amounts which are useful in radiation therapy. Several other examples of useful radioisotopes are disclosed in Good, U.S. Pat. No. 5,342,283, incorporated herein by reference. The radioactive isotope is applied to the carrier by techniques that are well known in the art.

In preferred embodiments, an improved brachytherapy seed of the present invention has both (a) a casing having a center of portion of a first diameter and end portions having a second diameter, wherein the second diameter is substantially smaller than the first diameter, and (b) a carrier having a polygonal cross section and having one end of the carrier rotated about the longitudinal axis of the carrier.

To demonstrate the improved seeds of the present invention, calculations were performed on various palladium-103 brachytherapy seeds to determine the relative amount of radiation that is emitted from the seeds in various directions. One seed had a standard present-day brachytherapy seed design, as depicted in FIG. 1, containing a palladium-103-laden copper carrier. The radiation emitted from this standard seed was compared to calculated amounts of radiation that would be emitted from a seed of the present invention. These calculations were based on a seed that is submerged in water, and a point along the longitudinal axis of the seed is selected. The relative intensity of the radiation emitted perpendicular to the longitudinal axis then is calculated. This corresponds to a calculation at a theta ($\theta$), i.e., an angle, of 90°. Calculations were made for a $\theta$ of 0° through 90° for relative intensity. A $\theta$ of 0° corresponds to radiation emitted from the end of the brachytherapy seed, i.e., radiation emitted parallel to the longitudinal axis of the carrier. In the following FIGS. 6–10, the plots show calculations of the relative radiation intensity attributed to primary photons, to radiation attributed to scatter in water, and total radiation.

Figure 6:
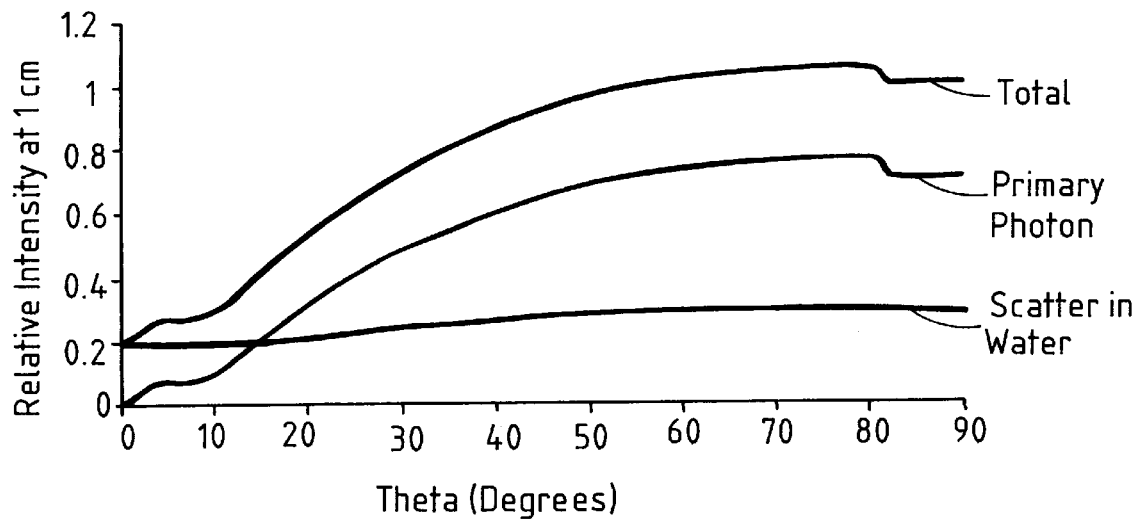
FIGS. 6–10 are plots of calculated relative radiation intensity vs. theta (degrees) for various brachytherapy seeds.

The plots in FIG. 6 illustrate the relative intensity for $\theta$ of 0° to 90° for a prior art palladium-103 seed having the configuration of FIG. 1. The carrier in the seed had a circular cross section. The plots in FIG. 6 show that the relative intensity of the radiation emitted from the end of the seed is about 20%, and rises in a relatively rapid fashion when $\theta$ is greater than about 10°.

Figure 7:
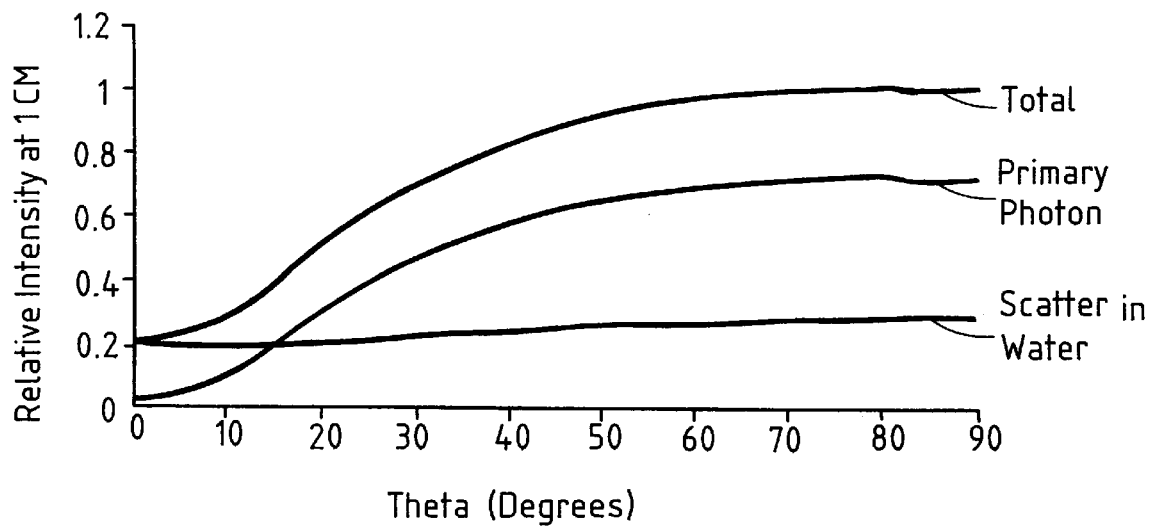

FIG. 7 illustrates the calculated relative radiation intensity for a palladium-103 brachytherapy seed having a casing as configured in FIG. 1, but containing a palladium-103-laden, copper-based carrier of square cross section having one end rotated 90° about the longitudinal axis of the carrier. The plots in FIG. 7 show that the calculated relative intensity of radiation emitted from the end of the seed is about 20%, and rises in a relatively rapid fashion even at $\theta$ of 0° to about 10°. The improvement in this seed is further illustrated at $\theta$ of about 80° to about 90°, wherein the calculated relative intensity of radiation does not decrease.

Figure 8:
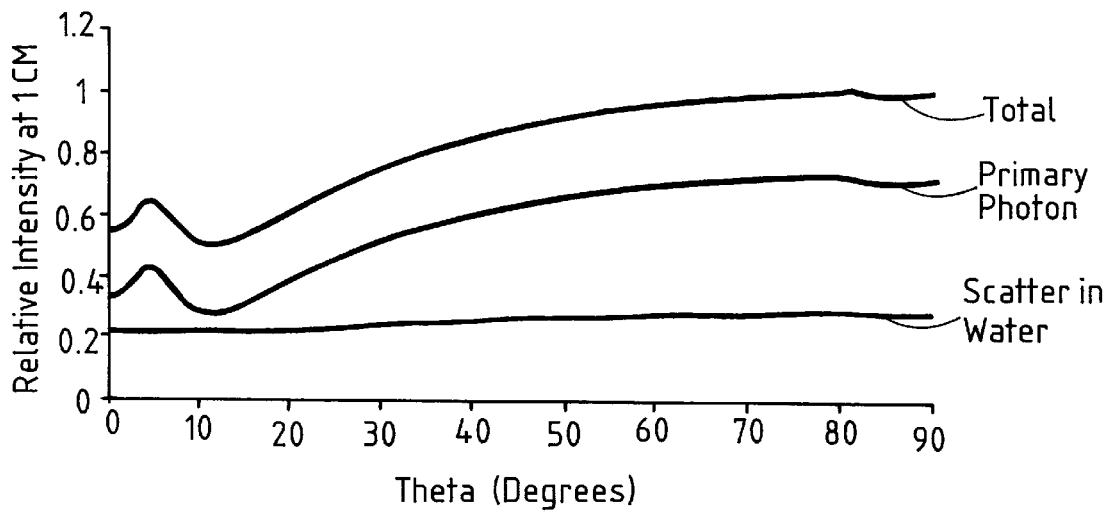
Figure 9:
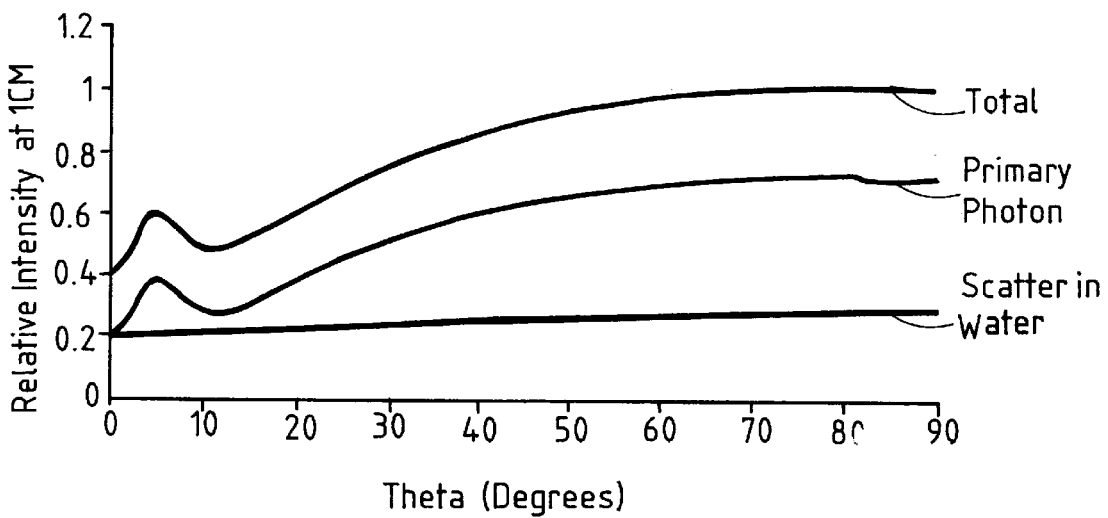
Figure 10:
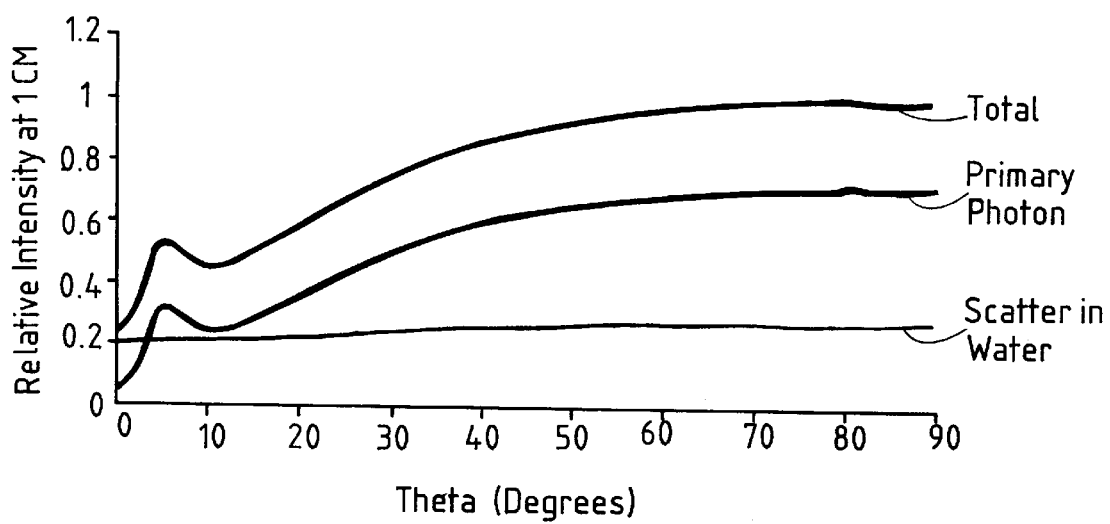

The calculations in the plots of FIGS. 8 through 10 show a further improvement provided by a palladium-103 seed containing a carrier of the present invention disposed in a casing having swaged end portions. In each of FIGS. 8–10, calculations were performed on a square copper wire carrier having a 0.05 cm (centimeter) diameter and a 0.3 cm length. In each of FIGS. 8–10, calculations were based on a titanium casing having an outer diameter of 0.08 cm, an inner diameter of 0.07 cm, and a length of 0.45 cm. The hypothetical seed used in the calculations for the plots of FIG. 8 had the end portions of the casing swaged such that the end had an outer diameter of 0.03 cm. Accordingly, the diameter of the end portions of the seed were reduced 62.5% compared to the diameter of the center portion of the casing.

The plots of FIG. 8 show that the calculated amount of radiation emitted from the end of the seed (i.e., $\theta$=0) has increased to about 55% relative intensity, and further significant increases are observed over $\theta$ of 0° to 10°. The calculations of the plots of FIGS. 9 and 10 further show that reductions in diameter of the end portions of seed of 50% and 37.5%, respectively, also provide improvements in uniformity of radiation emitting from brachytherapy seeds, especially at $\theta$ at 0° to about 20°.

Figure 11:
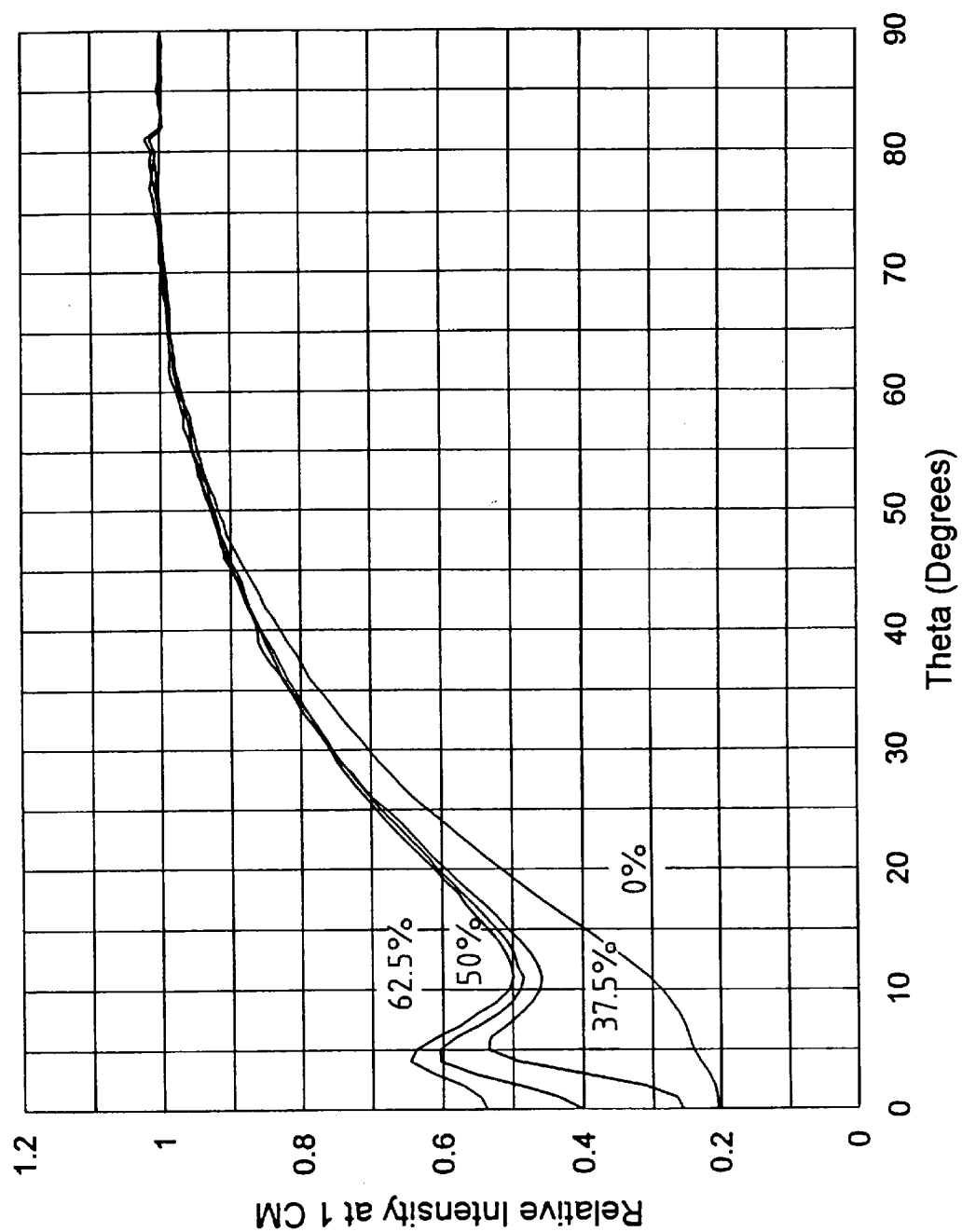
FIG. 11 contains comparative plots of calculated relative radiation intensity vs. theta (degrees) for various brachytherapy seeds.

FIG. 11 contains plots comparing the calculated relative intensity of radiation emitted from various casings. Calculations were performed for a hypothetical brachytherapy seed containing a palladium-103 laden copper carrier of square cross section and having one end rotated 90° about its longitudinal axis. FIG. 11 shows that a casing illustrated in FIG. 1 had a relative intensity of about 20° at $\theta$ of 0. In contrast, the present seeds had a relative intensity of about 25%, about 40%, and about 55% at $\theta$ of 0 for casings having a reduced end diameter of 32.5%, 50%, and 62.5%, respectively. The present seeds also demonstrates a dramatic increase in relative intensity over $\theta$ of 0° to 10°, and have a substantially higher relative intensity over the $\theta$ range of 0° to 40°. The plots of FIG. 11 illustrate the improved ability of a present casing to uniformly emit radiation generated by the radioisotope-laden carrier.

Obviously, many modifications and variations of the invention as hereinbefore set forth can be made without departing from the spirit and scope thereof, and, therefore, only such limitations should be imposed as are indicated by the appended claims.

What is claimed is:

1. An elongated brachytherapy seed comprising a radioisotope-laden carrier disposed within a sealed casing, wherein (a) the casing has a center portion of a first diameter and end portions each having a diameter that is substantially smaller than the first diameter, and (b) the radioisotope-laden carrier is acicular and has a polygonal cross section, wherein the carrier has one end of the carrier rotated around the longitudinal axis of the carrier.

2. An elongated brachytherapy seed comprising a radioisotope-laden carrier disposed within a sealed casing, said carrier having a polygonal cross section, and wherein one end of the carrier is rotated about 1° to about 180° around the longitudinal axis of the carrier.

3. The seed of claim 2, wherein one end of the carrier is rotated about 20° to about 150° around the longitudinal axis of the carrier.

4. The seed of claim 2, wherein one end of the carrier is rotated about 45° to about 120° around the longitudinal axis of the carrier.

5. The seed of claim 2, wherein the carrier has a trigonal, quadrilateral, pentagonal, or hexagonal cross section.

6. The seed of claim 5, wherein the carrier has a square, rectangular, or pentagonal cross section.

7. The seed of claim 2, wherein the carrier is acicular.

8. The seed of claim 2, wherein the carrier comprises a radioisotope adsorbed on a metal.

9. The seed of claim 8, wherein the metal comprises silver, copper, gold, or iron.

10. The seed of claim 8, wherein the radioisotope is a radioactive isotope of an element selected from the group consisting of iodine, palladium, cesium, gold, thulium, chromium, arsenic, yttrium, samarium, tantalum, radium, cobalt, iridium, and mixtures thereof.

11. The seed of claim 10, wherein the radioisotope is iodine-125 or palladium-103.

12. An elongated brachytherapy seed comprising a radioisotope-laden carrier disposed within a sealed casing, wherein (a) the casing has a center portion of a first diameter and end portions each having a diameter that is substantially smaller than the first diameter, wherein a radiation dose emanating from the center portion of the seed and the end portions of the seed is essentially uniform, and (b) the radioisotope-laden carrier is acicular and has a polygonal cross section.

13. An elongated brachytherapy seed comprising a radioisotope-laden carrier disposed within a sealed casing, said casing comprising a center portion having a first diameter and two end portions each having a diameter that is substantially smaller than the first diameter, wherein a radiation dose emanating from the center portion of the seed and the end portions of the seed is essentially uniform.

14. The seed of claim 13, wherein each diameter of the casing ends is about 25% to about 80% smaller than the first diameter of the casing center portion.

15. The seed of claim 13, wherein each diameter of the casing ends is about 35% to about 70% smaller than the first diameter of the center portion of the casing.

16. The seed of claim 13, wherein the diameters of each end portion are equal.

17. The seed of claim 13, wherein the diameters of each end portion are different.

18. The seed of claim 13, wherein the center portion of the casing is about 60% to about 80% of a total length of the casing.

19. The seed of claim 1 wherein the center portion of the seed is cylindrical in shape.

20. The seed of claim 1 wherein the casing comprises stainless steel, titanium, tantalum, a nickel alloy, a copper alloy, or an aluminum alloy.

21. The seed of claim 1 wherein the casing has a wall thickness of about 0.025 mm to about 0.127 mm.

22. The seed of claim 1 having an outer diameter of about 0.25 mm to about 1 mm.

23. The seed of claim 1 having a length of about 0.25 mm to about 25 mm.

* * * * *